US011039986B2

(12) United States Patent
Jain et al.

(10) Patent No.: US 11,039,986 B2
(45) Date of Patent: Jun. 22, 2021

(54) CHRONOTHERAPEUTIC DOSING OF MEDICATION AND MEDICATION REGIMEN ADHERENCE

(71) Applicant: Samsung Electronics Co., Ltd., Gyeonggi-Do (KR)

(72) Inventors: Jawahar Jain, Los Altos, CA (US); Cody Wortham, Mountain View, CA (US); James Young, Menlo Park, CA (US); Sajid Sadi, San Jose, CA (US); Pranav Mistry, Campbell, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 271 days.

(21) Appl. No.: 15/436,916

(22) Filed: Feb. 20, 2017

(65) Prior Publication Data

US 2017/0246086 A1  Aug. 31, 2017

Related U.S. Application Data

(60) Provisional application No. 62/299,987, filed on Feb. 25, 2016, provisional application No. 62/299,994, filed on Feb. 25, 2016.

(51) Int. Cl.
*A61J 7/04* (2006.01)
*A61B 5/021* (2006.01)
(Continued)

(52) U.S. Cl.
CPC ......... *A61J 7/0481* (2013.01); *A61B 5/02108* (2013.01); *A61B 5/4833* (2013.01);
(Continued)

(58) Field of Classification Search
CPC . A61B 5/021; A61B 5/02108; A61B 5/02405; A61B 5/02438; A61B 5/1113;
(Continued)

(56) References Cited

U.S. PATENT DOCUMENTS 5,618,665 A * 4/1997 Lurie ...................... C12Q 1/00
                                                        435/21
6,066,091 A  5/2000 Riviere et al.
(Continued)

FOREIGN PATENT DOCUMENTS

CN  101516255 A  8/2009
CN  101646471 A  2/2010
(Continued)

OTHER PUBLICATIONS

US 9,241,629, 5/2012, Sanpei et al. (withdrawn).
(Continued)

*Primary Examiner* — Omer S Khan
(74) *Attorney, Agent, or Firm* — Cuenot, Forsythe & Kim, LLC

(57) ABSTRACT

Chronotherapeutic dosing can include receiving, using a processor, sensor data from a sensor for a user, wherein the sensor data is collected subsequent to the user starting a regimen for a medication, determining, using the processor, a biological marker from the sensor data, wherein the biological marker is correlated with the medication, and comparing, using the processor, the biological marker with an expected state of the biological marker based upon a dose time of the medication. Chronotherapeutic dosing can also include providing, using the processor, a notification indicating a result of the comparing.

6 Claims, 3 Drawing Sheets

(51) Int. Cl.
  *G16H 50/70* (2018.01)
  *G16H 40/63* (2018.01)
  *G16H 20/13* (2018.01)
  *A61B 5/00* (2006.01)
  *A61B 5/16* (2006.01)
  *A61B 5/11* (2006.01)
  *A61B 5/024* (2006.01)

(52) U.S. Cl.
  CPC ............ *A61J 7/0418* (2015.05); *G16H 20/13* (2018.01); *G16H 40/63* (2018.01); *G16H 50/70* (2018.01); *A61B 5/021* (2013.01); *A61B 5/02405* (2013.01); *A61B 5/02438* (2013.01); *A61B 5/1113* (2013.01); *A61B 5/165* (2013.01); *A61B 5/4806* (2013.01)

(58) Field of Classification Search
  CPC ..... A61B 5/165; A61B 5/4806; A61B 5/4833; A61J 7/0418; A61J 7/0481; G16H 50/00
  See application file for complete search history.

(56) References Cited

U.S. PATENT DOCUMENTS

| | | |
|---|---|---|
| 6,332,100 B1 | 12/2001 | Sahai et al. |
| 6,832,200 B2 | 12/2004 | Greeven et al. |
| 7,108,680 B2 | 9/2006 | Rohr et al. |
| 7,122,005 B2 | 10/2006 | Shusterman |
| 8,556,865 B2 | 10/2013 | Krulevitch et al. |
| 8,961,414 B2 | 2/2015 | Teller et al. |
| 9,070,267 B2 | 6/2015 | Hanson et al. |
| 9,095,495 B2 | 8/2015 | Bogue |
| 9,110,836 B1 | 8/2015 | Fernandez |
| 9,131,903 B2 | 9/2015 | Tokita et al. |
| 9,189,739 B2 | 11/2015 | Mott et al. |
| 9,294,472 B2 | 3/2016 | Kim et al. |
| 9,301,712 B2 | 4/2016 | McNames et al. |
| 9,302,045 B2 | 4/2016 | Rule |
| 9,303,997 B2 | 4/2016 | McGavran et al. |
| 9,307,917 B2 | 4/2016 | Hong et al. |
| 9,308,319 B2 | 4/2016 | Mernoe et al. |
| 9,720,947 B2 | 8/2017 | Aron et al. |
| 10,722,179 B2 | 7/2020 | Pipke |
| 2007/0032733 A1* | 2/2007 | Burton ............... A61B 5/02405 600/509 |
| 2008/0312966 A1 | 12/2008 | Meshginpoosh |
| 2009/0109800 A1* | 4/2009 | Kimel ................... A61J 7/0481 368/10 |
| 2009/0192941 A1 | 7/2009 | Fournier et al. |
| 2009/0281518 A1 | 11/2009 | Ackermans et al. |
| 2010/0042043 A1* | 2/2010 | Krijnsen ............... A61M 5/142 604/66 |
| 2010/0106076 A1 | 4/2010 | Nissato et al. |
| 2010/0121156 A1 | 5/2010 | Yoo |
| 2010/0121314 A1* | 5/2010 | Lobbi ................. A61M 5/1723 604/890.1 |
| 2010/0160790 A1 | 6/2010 | Ibok |
| 2010/0185456 A1 | 7/2010 | Kansal |
| 2011/0087081 A1 | 4/2011 | Kiani et al. |
| 2011/0288380 A1 | 11/2011 | Inciardi et al. |
| 2013/0013333 A1 | 1/2013 | Gopinathan et al. |
| 2013/0041683 A1 | 2/2013 | Boissel et al. |
| 2013/0211204 A1 | 8/2013 | Caduff et al. |
| 2013/0245396 A1* | 9/2013 | Berman ............... G06F 19/3418 600/301 |
| 2014/0207048 A1 | 7/2014 | Dipierro et al. |
| 2014/0260985 A1 | 9/2014 | Akdogan et al. |
| 2014/0276549 A1 | 9/2014 | Osorio |
| 2014/0354435 A1 | 12/2014 | Hanson et al. |
| 2015/0199484 A1* | 7/2015 | Morris ................... G16H 20/10 705/2 |
| 2015/0223705 A1 | 8/2015 | Sadhu |
| 2015/0245201 A1 | 8/2015 | Kim et al. |
| 2015/0269342 A1 | 9/2015 | Swagger |
| 2016/0006788 A1 | 1/2016 | Martin et al. |
| 2016/0026773 A1 | 1/2016 | Chu et al. |
| 2016/0066828 A1 | 3/2016 | Phan et al. |
| 2016/0074583 A1 | 3/2016 | Hyde et al. |
| 2016/0128629 A1* | 5/2016 | Crow ................... A61B 5/6831 600/301 |
| 2017/0095184 A1* | 4/2017 | Heikenfeld .......... A61B 5/6831 |

FOREIGN PATENT DOCUMENTS

| | | | |
|---|---|---|---|
| CN | 101681455 A | 3/2010 | |
| CN | 102822834 A | 12/2012 | |
| CN | 102908130 A | 2/2013 | |
| EP | 2555676 A1 | 2/2013 | |
| EP | 2968075 A2 | 1/2016 | |
| JP | H08224308 A | 9/1996 | |
| KR | 20160063202 A | 6/2016 | |
| WO | 03081387 A2 | 10/2003 | |
| WO | 2011021163 A1 | 2/2011 | |
| WO | WO 2011021163 A1 * | 2/2011 | ............. G06F 19/00 |
| WO | 2015084352 A1 | 6/2015 | |
| WO | 2015095095 A2 | 6/2015 | |
| WO | 2015184084 A2 | 12/2015 | |
| WO | 2015189107 A1 | 12/2015 | |
| WO | 2016064266 A2 | 4/2016 | |

OTHER PUBLICATIONS

WIPO Int'l. Appln. No. PCT/KR2017/002070, International Search Report, dated May 23, 2017, 3 pg.
WIPO Int'l. Appln. No. PCT/KR2017/002070, Written Opinion, dated May 23, 2017, 6 pg.
EPO Appln. 17756863.1, Extended European Search Report, dated Oct. 22, 2018, 11 pg.
EP Appln. 17756864.1, Communication Pursuant to Article 94(3), 6 pg.
EP Appln. 17756863.1, Communication Pursuant to Article 94(3) EPC, dated Sep. 17, 2020, 5 pg.
CN Appln. 201780013541.X, Notification of First Office Action, dated Aug. 4, 2020, 10 pg.
CN Application No. 201780013541, Second Office Action, dated Mar. 29, 2021, 11 pg.

* cited by examiner

CHRONOTHERAPEUTIC DOSING OF MEDICATION AND MEDICATION REGIMEN ADHERENCE

CROSS-REFERENCE TO RELATED APPLICATIONS

This application claims the benefit of U.S. Provisional Patent Application No. 62/299,987 filed Feb. 25, 2016, and U.S. Provisional Patent Application No. 62/299,994 filed on Feb. 25, 2016, both of which are fully incorporated herein by reference.

TECHNICAL FIELD

This disclosure relates to chronotherapeutic dosing of medications and to medication regimen adherence.

BACKGROUND

Many patients rely heavily upon medications for their health and well-being. Some patients, e.g., those suffering from severe medical conditions, must follow a strict regimen of one or more medications. Achieving an effective medication regimen for such patients can be challenging. Often, medication regimens are created based upon general guidelines and/or general assumptions that may not be valid or applicable to a particular patient. Adjusting the medication regimen usually entails a continual cycle of lab testing coupled with physician visits.

Patient adherence to a medication regimen is another area of significant concern. Many patients, for example, follow a medication regimen that may involve taking multiple medications at various different times each day. As the complexity of the medication regimen increases, so too does the likelihood that the patient will miss a dose of one or more medications throughout the day, thereby placing the patient at significant risk.

SUMMARY

One or more embodiments are directed to a system and/or apparatus for chronotherapeutic dosing. In one aspect, a system can include a sensor configured to generate sensor data, a memory storing instructions, and a processor coupled to the sensor and the memory, wherein the processor, in response to executing the instructions, is configured to initiate executable operations. The executable operations can include receiving sensor data from the sensor for a user, wherein the sensor data is collected subsequent to the user starting a regimen for a medication, determining a biological marker from the sensor data, wherein the biological marker is correlated with the medication, comparing the biological marker with an expected state of the biological marker based upon a dose time of the medication, and providing a notification indicating a result of the comparing.

One or more embodiments are directed to methods of chronotherapeutic dosing. In one aspect, a method can include receiving, using a processor, sensor data from a sensor for a user, wherein the sensor data is collected subsequent to the user starting a regimen for a medication, determining, using the processor, a biological marker from the sensor data, wherein the biological marker is correlated with the medication, and comparing, using the processor, the biological marker with an expected state of the biological marker based upon a dose time of the medication. The method can also include providing, using the processor, a notification indicating a result of the comparing.

One or more embodiments are directed to computer program products for chronotherapeutic dosing. In one aspect, a computer program product includes a computer readable storage medium having program code stored thereon. The program code is executable by a processor to perform operations. The operations can include receiving sensor data from a sensor for a user, wherein the sensor data is collected subsequent to the user starting a regimen for a medication, determining a biological marker from the sensor data, wherein the biological marker is correlated with the medication, comparing the biological marker with an expected state of the biological marker based upon a dose time of the medication, and providing a notification indicating a result of the comparing.

One or more embodiments are directed to systems and/or apparatus for evaluating adherence to a regimen for a medication. In one aspect, a system can include a sensor configured to generate sensor data, a memory storing instructions, and a processor coupled to the sensor and the memory, wherein the processor, in response to executing the instructions, is configured to initiate executable operations. The executable operations can include receiving sensor data from the sensor for a user, wherein the sensor data is collected subsequent to the user starting a regimen for a medication, determining an updated state of a biological marker and/or a physiological state from the sensor data, wherein the biological marker and/or a physiological state is correlated with the medication, and comparing the updated state of the biological marker and/or a physiological state with a baseline for the biological marker and/or a physiological state to detect a change in the biological marker and/or a physiological state. The executable operations can also include determining that the user missed a dose of the medication in response to detecting the change in the biological marker and/or a physiological state during a time period correlated with a dose time of the medication and providing a notification indicating a missed dose of the medication.

One or more embodiments are directed to methods of evaluating adherence to a regimen for a medication. In one aspect, a method can include receiving, using a processor, sensor data from the sensor for a user, wherein the sensor data is collected subsequent to the user starting a regimen for a medication, determining, using the processor, an updated state of a biological marker and/or a physiological state from the sensor data, wherein the biological marker and/or a physiological state is correlated with the medication, and comparing, using the processor, the updated state of the biological marker and/or a physiological state with a baseline for the biological marker and/or a physiological state to detect a change in the biological marker and/or a physiological state. The method can also include determining, using the processor, that the user missed a dose of the medication in response to detecting the change in the biological marker and/or a physiological state during a time period correlated with a dose time of the medication and providing, using the processor, a notification indicating a missed dose of the medication.

One or more embodiments are directed to computer program products for evaluating adherence to a regimen for a medication. In one aspect, a computer program product includes a computer readable storage medium having program code stored thereon. The program code is executable by a processor to perform operations. The operations can include receiving sensor data from the sensor for a user, wherein the sensor data is collected subsequent to the user starting a regimen for a medication, determining an updated state of a biological marker and/or a physiological state from the sensor data, wherein the biological marker and/or a physiological state is correlated with the medication, and comparing the updated state of the biological marker and/or a physiological state with a baseline for the biological marker and/or a physiological state to detect a change in the biological marker and/or a physiological state. The method can also include determining, using the processor, that the user missed a dose of the medication in response to detecting the change in the biological marker and/or a physiological state during a time period correlated with a dose time of the medication and providing a notification indicating a missed dose of the medication.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be taken to limit the invention to only the embodiments shown. Various aspects and advantages will become apparent upon review of the following detailed description and upon reference to the drawings.

DETAILED DESCRIPTION

Figure 1:
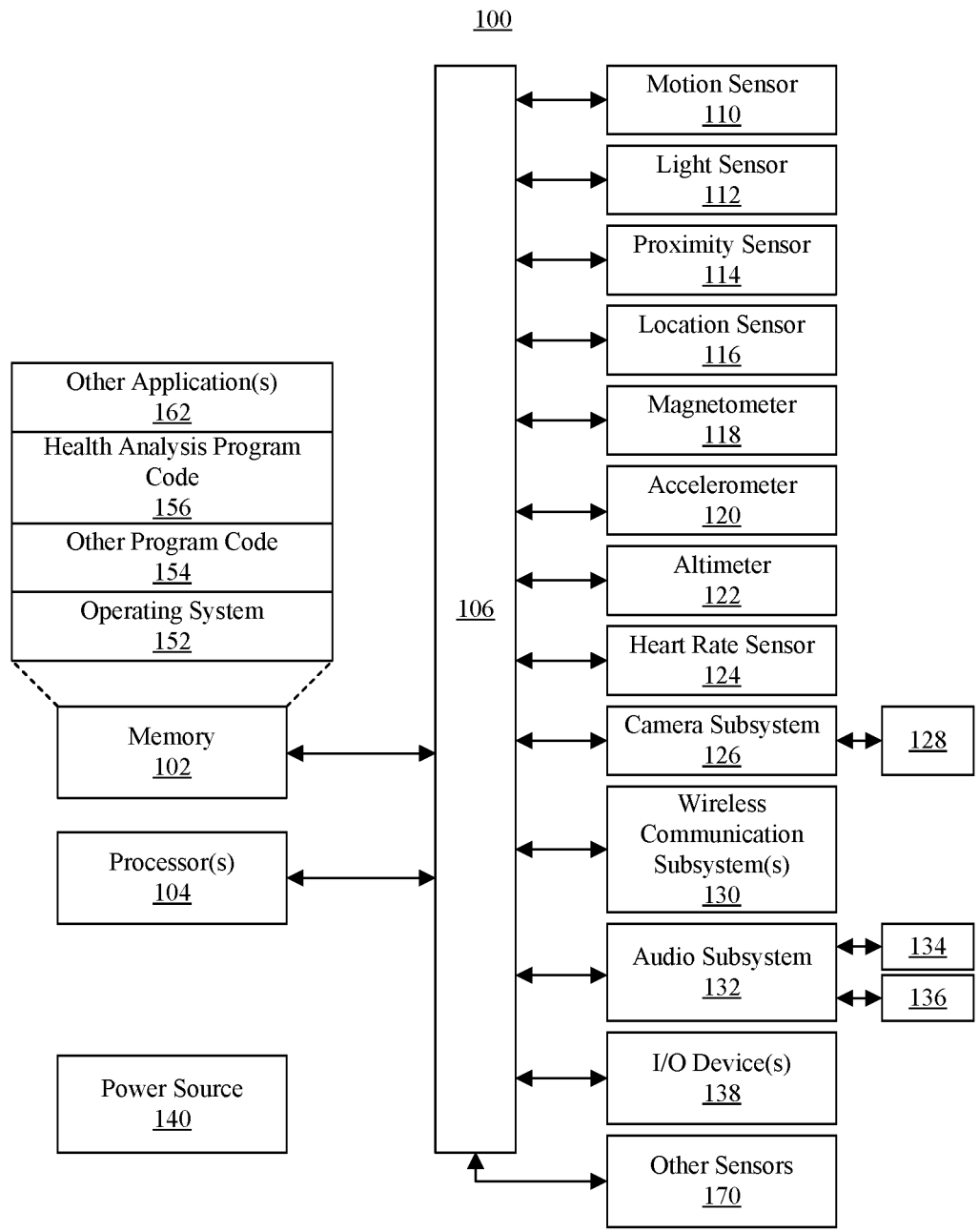
FIG. 1 illustrates an example system in accordance with one or more embodiments described herein.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to chronotherapeutic dosing of medications and to medication regimen adherence. Example embodiments disclosed within this disclosure provide methods, systems, and apparatus relating to chronotherapeutic dosing and detecting and/or monitoring medication regimen adherence. In general, a system is capable of establishing baselines for one or more biological markers of a user.

The system is capable of receiving sensor data for the user from a variety of different sensors over time. The system is capable of analyzing the sensor data to determine an updated or current state for one or more of the biological markers for the user. In one example, the system receives sensor data continuously in order to perform continuous monitoring of the state of the biological markers. For example, the system may receive sensor data subsequent to determining the baselines, subsequent to a change in the medication regimen, and/or in response to a trigger event or condition.

The system is capable of analyzing the biological markers with reference to the previously established baselines. The system is also capable of performing additional analysis. In one or more embodiments, the system is capable of analyzing the baselines and/or updated state of the biological markers relative to expected circadian-based trends in the human body. In one or more embodiments, the system is capable of analyzing the baselines and/or updated state of the biological markers relative to expected states of the biological markers. The expected states of the biological markers may reflect one or more characteristics of medications taken by the user as part of the medication regimen or a changed medication regimen being followed. The system is also capable of evaluating the baseline and/or updated state of the biological markers relative to the expected circadian variations and the characteristics of medications in the medication regimen for the user.

A circadian rhythm refers to a 24-hour cycle in the physiological processes of a human being. A variety of these physiological processes have been found to vary throughout this 24-hour cycle. For example, the body's production of hormones such as melatonin and cortisol vary throughout the day in accordance with the circadian rhythm of a human being. Production of these hormones can have a significant impact upon one's health and well-being.

In one or more embodiments, the system is capable of determining whether a user has missed a dose of a medication given the foregoing analysis. For example, the system is capable of analyzing the updated state of one or more biological markers determined from sensor data as described relative to the baselines. The system is capable of determining the likelihood that a user has missed a dose of a medication from a medication regimen based upon differences that may be detected between the baseline and the updated state of the biological markers. In example embodiments, the system is capable of providing the user with supplemental information as to how to address any missed dosages. The system is also capable of providing notifications, whether to the user or to medical personnel, relating to the user having missed a dosage of a medication.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example system 100 in accordance with one or more embodiments described within this disclosure. System 100 can include a memory 102, one or more processors 104 (e.g., image processors, digital signal processors, data processors, etc.), and interface circuitry 106. In one aspect, memory 102, processor(s) 104, and/or interface circuitry 106 are implemented as separate components. In another aspect, memory 102, processor(s) 104, and/or interface circuitry 106 are integrated in one or more integrated circuits. The various components in system 100, for example, can be coupled by one or more communication buses or signal lines (e.g., interconnects and/or wires). In one aspect, memory 102 may be coupled to interface circuitry 106 via a memory interface (not shown).

Sensors, devices, subsystems, and/or input/output (I/O) devices can be coupled to interface circuitry 106 to facilitate the functions and/or operations described within this disclosure including the generation of sensor data. The various sensors, devices, subsystems, and/or I/O devices may be coupled to interface circuitry 106 directly or through one or more intervening I/O controllers (not shown).

For example, motion sensor 110, light sensor 112, and proximity sensor 114 can be coupled to interface circuitry 106 to facilitate orientation, lighting, and proximity functions, respectively, of system 100. Location sensor 116 (e.g., a GPS receiver and/or processor) can be connected to interface circuitry 106 to provide geo-positioning sensor data. Electronic magnetometer 118 (e.g., an integrated circuit chip) can be connected to interface circuitry 106 to provide sensor data that can be used to determine the direction of magnetic North for purposes of directional navigation. Accelerometer 120 can be connected to interface circuitry 106 to provide sensor data that can be used to determine change of speed and direction of movement of a device in 3-dimensions. Altimeter 122 (e.g., an integrated circuit) can be connected to interface circuitry 106 to provide sensor data that can be used to determine altitude. Heart rate sensor 124 can be connected to interface circuitry 106 to generate sensor data and facilitate measurement of a heartbeat and the determination of a heart rate.

Camera subsystem 126 can be coupled to an optical sensor 128. Optical sensor 128 can be implemented using any of a variety of technologies. Examples of optical sensor 128 can include, but are not limited to, a charged coupled device (CCD), a complementary metal-oxide semiconductor (CMOS) optical sensor, etc. Camera subsystem 126 and optical sensor 128 can be used to facilitate camera functions, such as recording images and/or video clips (hereafter "image data"). In one aspect, image data is a subset of sensor data.

Communication functions can be facilitated through one or more wireless communication subsystems 130. Wireless communication subsystems 130 can include, but are not limited to, radio frequency receivers and transmitters, optical (e.g., infrared) receivers and transmitters, and so forth. The specific design and implementation of wireless communication subsystem 130 can depend on the particular type of system 100 implemented and/or the communication network(s) over which system 100 is intended to operate.

For purposes of illustration, wireless communication subsystem(s) 130 may be designed to operate over one or more mobile networks (e.g., GSM, GPRS, EDGE), a WiFi network which may include a WiMax network, a short range wireless network (e.g., a Bluetooth network), and/or any combination of the foregoing. Wireless communication subsystem(s) 130 can implement hosting protocols such that system 100 can be configured as a base station for other wireless devices.

Audio subsystem 132 can be coupled to a speaker 134 and a microphone 136 to facilitate voice-enabled functions, such as voice recognition, voice replication, digital recording, audio processing, and telephony functions. Audio subsystem 132 is capable of generating audio type sensor data. In one or more embodiments, microphone 136 may be utilized as a respiratory sensor.

I/O devices 138 can be coupled to interface circuitry 106. Examples of I/O devices 138 can include, but are not limited to, display devices, touch sensitive display devices, track pads, keyboards, pointing devices, communication ports (e.g., USB ports), network adapters, buttons or other physical controls, and so forth. A touch sensitive device such as a display screen and/or a pad is configured to detect contact, movement, breaks in contact, etc., using any of a variety of touch sensitivity technologies. Example touch sensitive technologies include, but are not limited to, capacitive, resistive, infrared, and surface acoustic wave technologies, other proximity sensor arrays or other elements for determining one or more points of contact with a touch sensitive device, etc. One or more of I/O devices 138 may be adapted to control functions of sensors, subsystems, and such of system 100.

System 100 further includes a power source 140. Power source 140 is capable of providing electrical power to the various elements of system 100. In an embodiment, power source 140 is implemented as one or more batteries. The batteries may be implemented using any of a variety of different battery technologies whether disposable (e.g., replaceable) or rechargeable. In another embodiment, power source 140 is configured to obtain electrical power from an external source and provide power (e.g., DC power) to the elements of system 100. In the case of a rechargeable battery, power source 140 further may include circuitry that is capable of charging the battery or batteries when coupled to an external power source.

Memory 102 can include random access memory (e.g., volatile memory) and/or non-volatile memory, such as one or more magnetic disk storage devices, one or more optical storage devices, flash memory, etc. Memory 102 can store operating system 152, such as LINUX, UNIX, a mobile operating system, an embedded operating system, etc. Operating system 152 may include instructions for handling system services and for performing hardware dependent tasks.

Memory 102 may also store other program code 154. Examples of other program code 154 may include instructions to facilitate communicating with one or more additional devices, one or more computers and/or one or more servers; graphic user interface processing; processing instructions to facilitate sensor-related functions; phone-related functions; electronic-messaging related functions; Web browsing-related functions; media processing-related functions; GPS and navigation-related functions; security functions; camera-related functions including Web camera and/or Web video functions; and so forth. Memory 102 may also store one or more other application(s) 162.

Memory 102 may store health analysis program code 156. In one aspect, health analysis program code 156 is adapted to facilitate chronotherapeutic dosing of medications for a user. In another aspect, health analysis program code 156 is adapted to evaluate medication regimen adherence for a user (e.g., detecting whether a user has missed a dose of one or more medications). Health analysis program code 156 is capable of establishing baselines using sensor data, analyzing further received sensor data, querying a user for input, querying one or more external data sources for information, and performing comparisons of sensor data, user input, baselines, data obtained from the external data sources, and/or other internally stored data. In one or more embodiments, health analysis program code 156 facilitates the real time performance of one or more or all of the operations described herein. Further aspects of operations performed through execution of health analysis program code 156 are described herein with reference to the remaining figures.

Memory 102 may also store various types of data (not shown) such as sensor data, baseline data including baselines for one or more biological markers, data obtained by way of received user input(s), and/or data obtained by way of querying one or more external data sources.

The various types of instructions and/or program code described are provided for purposes of illustration and not limitation. The program code may be implemented as separate software programs, procedures, or modules. Memory 102 can include additional instructions or fewer instructions. Furthermore, various functions of system 100 may be implemented in hardware and/or in software, including in one or more signal processing and/or application specific integrated circuits.

Program code stored within memory 102 and any data items used, generated, and/or operated upon by system 100 are functional data structures that impart functionality when employed as part of the device. Further examples of functional data structures include, but are not limited to, sensor data, data obtained via user input, data obtained via querying external data sources, baseline information, and so forth. The term "data structure" refers to a physical implementation of a data model's organization of data within a physical memory. As such, a data structure is formed of specific electrical or magnetic structural elements in a memory. A data structure imposes physical organization on the data stored in the memory as used by a processor.

In one or more embodiments, one or more of the various sensors and/or subsystems described with reference to system 100 may be separate devices that are coupled or communicatively linked to system 100 through wired or wireless connections. For example, one or more or all of motion sensor 110, light sensor 112, proximity sensor 114, location sensor 116, magnetometer 118, accelerometer 120, altimeter 122, heart rate sensor 124, camera subsystem 125, audio subsystem 132, and so forth may be implemented as separate systems or subsystems that couple to system 100 by way of I/O devices 138 and/or wireless communication subsystem(s) 130.

One or more of the sensors may be worn directly by the user and provide data to system 100 via a wired or wireless connection. Examples of additional sensors that are not illustrated in FIG. 1, but which may be used and/or worn by a user to provide sensor data to system 100 can include, but are not limited to electrocardiography (ECG) sensors, photoplethysmography (PPG) sensors, gyroscopes, respiratory sensors, galvanic skin response (GSR) sensors, etc. These additional sensors are represented in FIG. 1 by "other sensors" block 170. In one or more embodiments, sensors and/or subsystems as described herein are configured to generate sensor data that is stored in a memory external to system 100. In that case, system 100, e.g., processors 104, may access the sensor data for use and/or analysis as described herein.

System 100 may include fewer components than shown or additional components not illustrated in FIG. 1 depending upon the particular type of system that is implemented. In addition, the particular operating system and/or application(s) and/or other program code included may also vary according to system type. Further, one or more of the illustrative components may be incorporated into, or otherwise form a portion of, another component. For example, a processor may include at least some memory.

System 100 is provided for purposes of illustration and not limitation. A device and/or system configured to perform the operations described herein may have a different architecture than illustrated in FIG. 1. The architecture may be a simplified version of system 100 and include a processor and memory storing instructions. The architecture may include one or more sensors as described herein. System 100, or a system similar to system 100, is capable of collecting data using the various sensors of the device or sensors coupled thereto. It should be appreciated, however, that system 100 may include fewer sensors or additional sensors. Within this disclosure, data generated by a sensor is called "sensor data."

Examples implementations of system 100 may include, but are not to limited to, a smart phone or other mobile device or phone, a wearable computing device (e.g., smart watch, fitness tracker, patch, etc.), a dedicated medical device, a computer (e.g., desktop, laptop, tablet computer, other data processing system, etc.), and any suitable electronic device capable of sensing and processing the sensor data. Furthermore, it will be appreciated that embodiments can be deployed as a standalone device or deployed as multiple devices in a distributed client-server networked system. In an example embodiment, a smart watch or fitness tracker may be paired to operate with a mobile phone. The mobile phone may or may not be configured to interact with a remote server and/or computer system.

Figure 2:
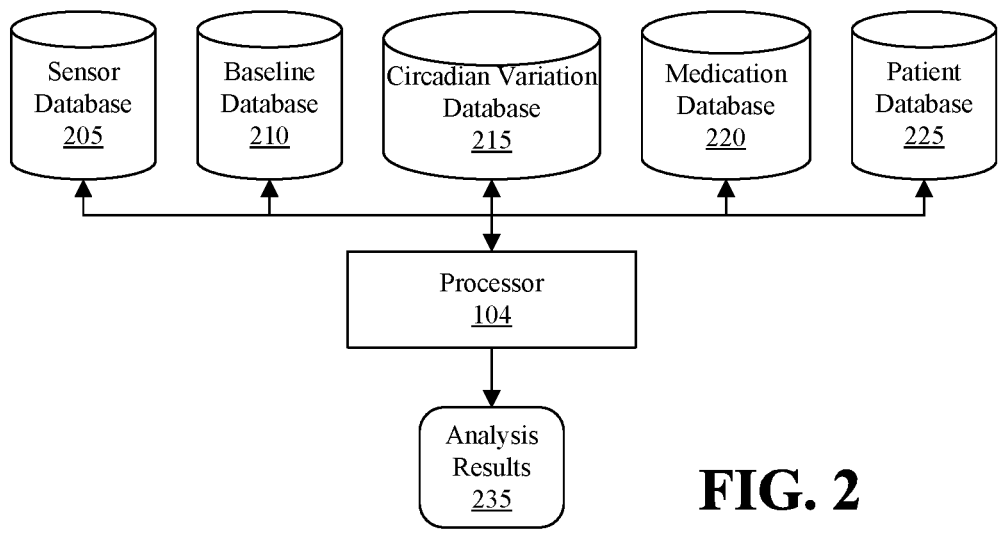
FIG. 2 illustrates example data processing operations performed by a system as described herein in connection with FIG. 1.

FIG. 2 illustrates example data processing operations performed by a system as described herein in connection with FIG. 1. Within a memory, e.g., memory 102, the system is capable of storing sensor data within a sensor database 205, baselines within a baseline database 210, and circadian variation data within a circadian variation database 215. The system is further capable of accessing medication characteristics from a medication database 220 and patient data from a patient database 225. In one aspect, medication database 220 and/or patient database 225 are stored within the system, e.g., in memory 102. In another aspect, medication database 220 and/or patient database 225 are stored within another data storage device external to the system. In that case, the system is capable of querying the database(s) to obtain the information contained therein.

It should be appreciated that while certain types of data are described as being stored within a database, the inventive arrangements are not intended to be limited to storing data in one particular format or another. For example, the various types of data described within this disclosure may be stored in any of a variety of different types of data storage devices, in any of a variety of different data structures, e.g., files, markup languages, and the like.

Sensor data is received from one or more different sensors as described with reference to FIG. 1 and stored in memory. Processor 104 is capable of analyzing sensor data from sensor database 205 to generate baselines stored in baseline database 210. In one aspect, baselines are biological markers for a user, determined from sensor data, where the user is in a known or controlled state. In one or more embodiments, baselines are determined prior to the user beginning any medication regimen. In that case, baselines reflect the states of the biological markers for the user prior to the user taking medication or beginning a medication regimen. In one or more embodiments, baselines are determined while the user is adhering to, or following, a particular medication regimen. Thus, in the latter case, baselines reflect the state of biological markers for the user while the user is taking one or more medications as prescribed in accordance with the medication regimen. In one or more embodiments, the baselines may be one or more baseline physiological state(s) of a user as determined from the sensor data.

The term "medication regimen," as used herein, refers to the overall medication program followed by a user. For example, the medication regimen may specify information such as the particular medication(s) taken by the user, the quantity and/or the concentration of each medication taken by the user, the times of day and/or frequency that the medications are taken by the user, etc. Within this disclosure, the terms "regimen" and "medication regimen" are used interchangeably from time-to-time.

For purposes of illustration, a user may be wired or coupled to one or more wearable sensors. These sensors may include, but are not limited to, ECG sensors, PPG sensors, respiration sensors, accelerometers, gyroscopes, GSR sensor, other sensors described herein, etc. Using these sensors, the system is able to capture, e.g., store, sensor data and determine biological markers from the sensor data.

Examples of biological markers that the system may determine from sensor data include, but are not limited to, heart rate, stress, heart rate variability, arrhythmia, respiration, activity levels, sleep, stress, mood, tone of voice, total activity (e.g., particular movements, activities, and types of movement such as gait), blood pressure, etc. Certain biological markers are determined directly from sensor data from particular sensors. For example, heart rate and/or heart rate variability may be determined directly from sensor data from a heart rate sensor. The system is also capable of determining other biological markers from sensor data from a plurality of different sensors. The following is a brief description of additional biological markers and/or physiological states that the system is capable of determining from sensor data. The system is capable of determining a baseline for each of these additional biological markers and/or physiological states.

In an embodiment, the system is capable of determining sleep patterns as a biological marker. The system is capable of determining sleep patterns, e.g., quality of sleep, using one or more sensors. In an example, the system is capable of measuring sleep of the user using heart rate data and accelerometer data. The system is capable of determining the amount of time that the user sleeps each night, quality of sleep, and so forth as a baseline.

In an embodiment, the system is capable of detecting stress in the user as a biological marker. When under stress, for example, the user's adrenergic nervous system (ANS) arousal and valence are typically in the second quadrant of the Circumplex Model of Emotions, which can be determined by heart rate and heart rate variability analysis where both trend down at the same time. In one embodiment, the system is capable of using heart rate and heart rate variability to determine whether the user is under stress and/or the amount of stress.

For example, the system is capable of determining whether the user is subject to stress and whether the amount of stress exceeds a baseline or threshold amount of stress based upon heart rate (e.g., energy) and heart rate variability (e.g., mood) of the user both being low (e.g., below a threshold heart rate and/or a threshold heart rate variability) at the same time and/or remaining low (concurrently) for at least a minimum amount of time. The thresholds used may be specific to the user or generalized across one or more different users. Responsive to determining that the heart rate and heart rate variability both are low for at least the minimum amount of time, for example, the system determines that the user is experiencing stress. The system is capable of determining a baseline for stress for the user.

In an embodiment, the system is capable of determining mood and/or detecting depression as a biological marker. In one example, the system is capable of detecting mood and/or depression by analyzing the tone (e.g., and modulation) of the user's voice. The system, for example, is capable of detecting crying, supplicatory speech, apathic (disinterested) syndrome, length in time of pauses, (average) vocal pitch, mean loudness, and/or variation of loudness over time. Responsive to determining one or more of the characteristics of the user's voice noted herein, the system is capable of determining that the user likely suffers from depression.

In another aspect, the system is also capable of detecting depression in the user based upon heart rate and heart rate variability. For example, covariance between heart rate and heart rate variability may be used to detect the presence of depression in the user. Further, the system is capable of receiving user inputs indicating mood and/or depression. In any case, the system is capable of determining a baseline for depression and/or mood.

In an embodiment, the system is capable of determining blood pressure, e.g., systolic blood pressure, based upon PPG morphology. The system, for example, is capable of determining systolic blood pressure for a user based upon the area beneath the curve of a PPG waveform. Greater area beneath the PPG waveform coincides with greater systolic blood pressure. Thus, in using the PPG morphology, a blood pressure sensor is not required.

In an embodiment, the system is capable of analyzing accelerometer data to determine the energy expended by a user. The energy expended may be measured in terms of power output of the accelerometer. Further, the accelerometer data may be analyzed to detect and/or recognize particular movements and/or motions as performed by the user. The system is capable of determining a baseline for energy expended (e.g., total activity of the user).

The system is capable of generating baselines to specify values for the various biological markers described herein. In one or more embodiments, the system is capable of collecting sensor data continuously, e.g., 24 hours a day and/or 7 days a week, and storing such data within sensor database 205. The system is capable of sampling the sensor data at specified intervals of 30 seconds, 1 minute, 2 minutes, etc. thereby providing continuous or nearly continuous monitoring of the user. The system is capable of calculating a baseline for each of the various biological markers described herein. A baseline may be a value, a range of values, a mean, a trend, etc. for the various biological markers discussed. Further, the baseline may be specified for one or more different times throughout the day, different segments of the day, etc. As such, a baseline can be correlated with particular points during the circadian cycle of user. In this regard, the system is capable of correlating baselines with different times and/or segments of the circadian cycle for a user.

Consider a user that is taking, or is anticipated to take, a medication that affects ANS such as a beta blocker. For such a user, examples of baselines that may be generated for the user and stored in baseline database 210 may include baselines for biological markers such as heart rate, heart rate variability, stress, mood, depression, PPG morphology, blood pressure, sleep, movements, total activity, etc. for various times and/or segments of the day.

Other baselines that the system is capable of determining may be generated from data entered by the user. For example, the user may enter data as a log of activities such as intake of fluids, salt, and/or other items throughout the day. The user may enter the data into a user interface provided by the system in executing health analysis program code 156. As an illustrative example, the system may present the user with a user interface through which the user may enter such information throughout the day for purposes of generating baselines.

Circadian variation data stored in circadian variation database 215 specify expected effects on one or more biological markers for different times throughout the day. Biological markers may be expected to increase, decrease, or remain unchanged in accordance with the location in the Circadian cycle that the biological markers are measured. Circadian variation data specify, on a per biological marker basis, whether the biological marker is expected to increase, decrease, or remain the same for various times and/or time periods throughout the day.

For example, blood pressure and heart rate can be synchronized in a predictable manner with the circadian rhythm and the rhythm of the user's activity-rest cycle. These variations may be specified in circadian variation data and correlated with time for purposes of comparison with blood pressure and/or heart rate biological markers determined from sensor data for the user. A number of other physiological functions such as renal, cardiovascular, gastrointestinal, and endocrinological functions also can undergo a circadian pattern (e.g., variation) that may also be specified in circadian variation database 215. These circadian variations can influence blood pressure, absorption, metabolism, and elimination of medications from the body, including antihypertensive medications.

In another example, the peak function of GFR and renal plasma flow are reached during the day time with the minimums occurring at night. Thus, medications are cleared from the body more efficiently during the day time than at night. Likewise, the molecular clock that controls the circadian rhythm affects various pathways that are also responsible for release of catecholamines that are responsible for fight or flight syndrome. The release of such catecholamines can also be circadian in nature with the peak occurring in the morning. This leads to higher blood pressure during morning hours. Similarly, there is a cortisol awakening response (CAR) that leads to a higher secretion of cortisol in the morning. This phenomenon aids one in waking up for daily activities. Cortisol further sensitizes the beta-adrenergic receptors of the body to the effect of these catecholamines such as epinephrine and norepinephrine.

Another circadian variation is a pronounced dip in heart rate and blood pressure during the night. During the night, the dip occurs so as to allow the body to conserve metabolic processes, rest, and recuperate. Due to the foregoing reasons, there can be a pronounced surge of blood pressure in the morning, called morning surge reactivity.

Circadian variation database 215 specifies these expected circadian variations such as morning surge reactivity and dipping in blood pressure and heart rate during the night. Circadian variation database 215 may be used by processor 104 to characterize results as being consistent with expectations, e.g., within a specified tolerance considered normal given circadian variations in the biological markers.

Medication database 220 stores characteristics for a plurality of different medications. Examples of the characteristics include, but are not limited to, the half-life of each medication. In an embodiment, the half-life information may be specified as a range or continuum based upon patient age and/or other concomitant medications. Medication database 220 may also specify known side effects, drug-to-drug interactions between medications, and so forth. Drug-to-drug interactions, for example, may influence how quickly a given medication is cleared from the body.

Patient database 225 may specify user-specific data. For example, patient database 225 may specify a particular regimen for a user, patient side effects to medications, and so forth. In another aspect, patient database 225 may specify expected values, ranges, and/or states for biological markers that are specific to the user. Such expected values, ranges, and/or states may represent desired values, ranges, and/or states for biological markers indicating that the user is in good health or is responding to a medication regimen as expected.

In an embodiment, patient database 225 is capable of storing data entered or provided by a user. For example, the user may enter information as part of an activity log. The user may enter data such as the time that one or more medications are consumed. The system is capable of storing such user entered data within patient database 225.

In any case, processor 104 is capable of operating on sensor data to generate one or more baselines within baseline database 210 for the user. Processor 104 further may continue to operate on newly received sensor data to determine updated states of the biological markers for purposes of comparing with the baselines.

In one or more embodiments, processor 104 is capable of comparing current states of biological markers with baseline biological markers, comparing current state of biological markers with expected values (e.g., states) for biological markers, comparing current state of biological markers with expected values and/or states for biological markers as adjusted according to circadian variations, and/or considering medication characteristics from medication database 220 and patient data from patient database 225 as described herein in greater detail. Results generated by processor 104 are output as analysis results 235. Analysis results 235 may be stored in memory, provided as a notification to the user, provided as a notification to a medical provider (e.g., a device or system of a medical provider), etc.

In one or more embodiments, a system as described in connection with FIG. 1 is adapted to facilitate the creation of a chronotherapeutic dosing regimen. The dosing regimen is effective in suppressing blood pressure, heart rate, and/or other physical phenomena. The dosing regimen is also effective in re-creating various physical phenomena. For example, a dosing regimen developed by the system is effective in recreating the dipping phenomenon in the night relating to blood pressure and/or heart rate in the event that such physical phenomena are missing in the user in order to reduce health risks.

As an illustrative example, a patient taking antihypertensive medications may be instructed to take medications during the morning period. The morning may be a time period to which the dosing period is biased. Different antihypertensive medications, however, control various aspects of the blood pressure mechanism. Some medications exhibit higher benefit when taken by the patient at certain time intervals of the diurnal cycle. For example, renin-angiotensin-aldosterone inhibitors deal with the renin angiotensin system (RAS) system, which is more active during the night time. Further compounding the problem, medications may have dramatically different half-lives. For example, diuretic chlorthalidone has a much longer half-life than diuretic hydrochlorothiazide. Medications may also have different elimination mechanisms. In consequence, a particular medication may no longer be in the patient's body at the precise time when the medication would be of most benefit to the user.

Accordingly, a system as described herein is capable of analyzing a dosing regimen to produce an effect on the body of the user that addresses the circadian patterns of different bodily systems and functions to improve the effects of medication(s) taken by the user. The system may be applied to users taking medications for any of a variety of different conditions. These conditions may include or relate to cardiac functions, epileptic seizure, headaches, allergic reactions, response to infection, rhinitis, arthritis, sickle cell anemia, hemorrhage, perforated ulcer, dermatoses, chronic pain, epileptic seizure, peptic ulcer disease exacerbation, asthma, and so forth. The list of conditions provided herein is not intended to be exhaustive, but merely to provide illustrative examples.

Figure 3:
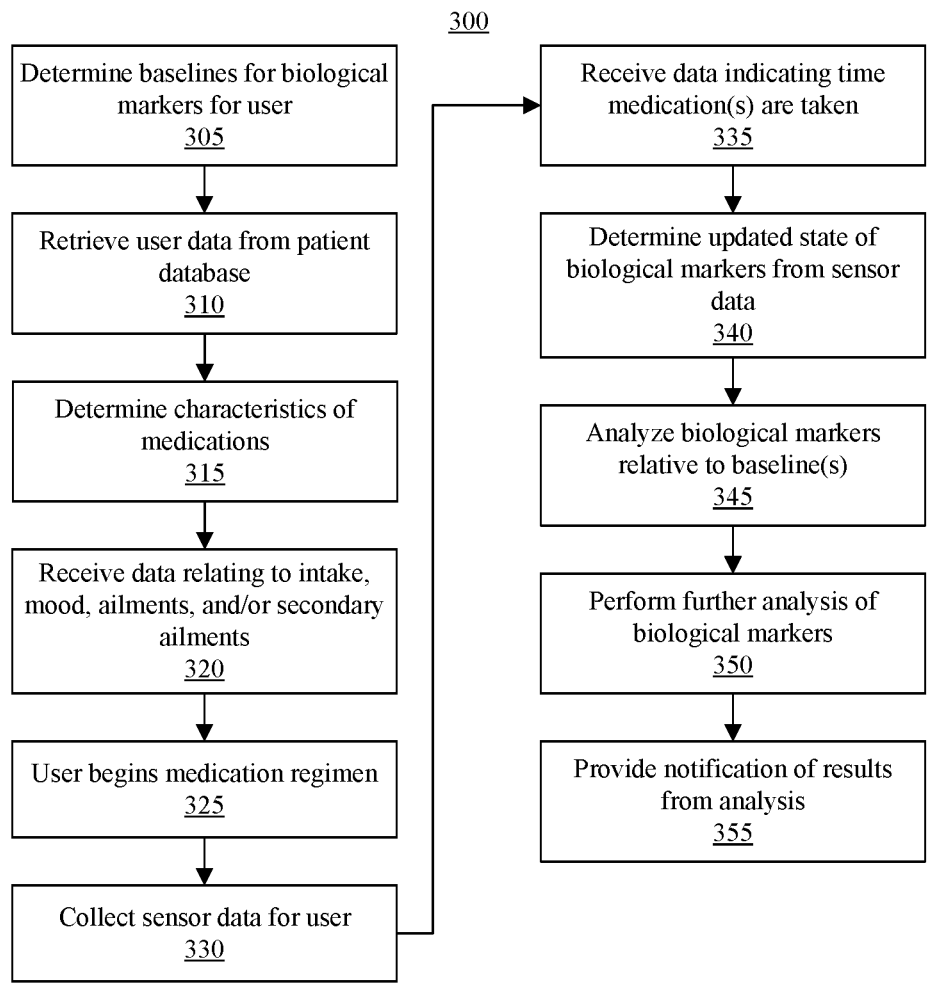
FIG. 3 illustrates an example method of chronotherapeutic dosing.

FIG. 3 illustrates an example method 300 of chronotherapeutic dosing. Method 300 may be performed by a system the same as or similar to the system described in connection with FIG. 1. A system as described herein is capable of evaluating the medication regimen of a user to determine effectiveness. In an aspect, effectiveness of the medication regimen may be determined based, at least in part, upon a comparison of biological markers determined from sensor data with baseline biological markers and/or circadian variations in the biological markers.

In block 305, the system is capable of determining baselines for one or more biological markers. The system is capable of determining baselines for one or more biological markers as discussed in connection with FIG. 2. Once determined, the system stores the baselines for the biological markers within a memory for subsequent use. In one or more embodiments, baseline determination is optional. For example, in cases where biological markers are determined from sensor data (e.g., continuously and/or in real time), the system may compare the biological markers with expected states of the biological markers. Accordingly, determination of baselines may or may not be used depending upon the particular comparisons that are performed by the system.

In block 310, the system is capable of retrieving user data from the patient database. For example, the system is capable of retrieving a stored medication regimen. The medication regimen may specify each medication to be taken by the user including concomitant medications. As part of the patient data that is retrieved, the system is capable of retrieving age of the user, and the like.

In block 315, the system determines characteristics of the medications listed in the medication regimen. For example, the system accesses, e.g., queries, a medication database to obtain characteristics for each of the medications specified on the medication regimen. In one example, the system retrieves a half-life for each medication listed on the regimen from the medication database. In one or more embodiments, half-lives of medications are specified in the medication database for medications for various patient ages and/or for concomitant medicines since patient age and/or concomitant medicines can influence half-life. In another example, the system retrieves drug-to-drug interaction information and/or drug clearance information from the medication database for the drugs specified on the medication regimen for the user.

In block 320, the system optionally receives data relating to a variety of different factors. For example, the system is capable of providing further user interfaces through which the user may provide inputs specifying data indicating health and/or suffering of the user. In one or more embodiments, the system is capable of prompting the user for the data. In another embodiment, the system is capable of providing user interfaces to receive data in response to a user request to do so. The data that is received may be stored internally in the system and/or in the patient database.

For example, through the user interface, the system is capable of receiving data specifying intake amounts of various items throughout the day such as fluid intake, salt-intake (e.g., low, moderate, high), etc. Through the user interface, the system may receive data specifying the user's mood via an accepted mood scale for, or corresponding to, the circadian segments of the day that are being analyzed by the system. Through the user interface, the system is capable of receiving data specifying a number of ailments that the user expects medications from the regimen to alleviate or otherwise address. Through the user interface, the system is capable of receiving data specifying secondary ailments that the user may be experiencing. Secondary ailments refer to side-effects of medications including side-effects of drug-to-drug interactions.

In block 325, the user begins the medication regimen. In one or more embodiments, the system may receive an input from the user via a user interface generated by the system indicating that the user has started the medication regimen. In block 330, the system is capable of collecting sensor data for the user. As discussed, the system is capable of collecting sensor data continuously throughout the day over many days. For example, the system is capable of collecting sensor data 24 hours a day and/or 7 days a week, at particular intervals, etc.

In block 330, the system receives data indicating a time when medication(s) are taken by the user. In one or more embodiments, the system is capable of providing a user interface through which the user is able to provide one or more user inputs. The user inputs specify data such as the particular medication(s) taken and the time that the medication(s) are taken (e.g., a dose time). The data that is received may be stored internally in the system and/or in the patient database. The system may receive data indicating times of taken doses of medications throughout the time that the system monitors the user. The system is capable of correlating user provided data, like sensor data, with time, e.g., timestamped, for storage. In one or more other embodiments, the system is capable of reading the times that medications are to be taken from the medication regimen.

In block 340, the system is capable of determining an updated state of one or more biological markers from the sensor data. The system is capable of determining one or more biological markers indicative of the state of the user's health from the sensor data. For example, the system is capable of determining one or more biological markers relating to the state of the user's ANS. Examples of biological markers determined by the system include, but are not limited to, heart rate, blood pressure, change in the trend of blood pressure, stress, sleep, respiratory activity, mood, depression, and so forth. In one aspect, the system is capable of determining blood pressure based upon the PPG morphology of the user. It should be appreciated that the system is capable of determining an updated state for any of the biological markers described herein that may be used as baselines.

In block 345, the system is capable of analyzing the biological markers, e.g., the updated states of the biological markers, relative to the baselines. The system is capable of comparing the updated state of one or more of the biological markers with the same respective baselines. In one aspect, the system determines whether a statistically significant change is detected. For example, the system may determine whether the updated state of the biological marker has changed, e.g., improved or worsened, more than a threshold amount compared to the relevant, e.g., same, baseline. In one aspect, the circadian variation in the biological marker may be incorporated into the comparison.

In block 350, the system is capable of performing further analysis of the biological markers. In one or more embodiments, the system is capable of analyzing the biological markers (e.g., the updated states of the biological markers) and/or baselines relative to expected circadian variations, characteristics of medications, expected states of the biological markers, and/or user provided data. In one aspect, the system is capable of determining whether the updated state of a biological marker is within an acceptable range for the respective biological marker given circadian variations that are applicable to the biological marker.

As an illustrative example, the system is capable of comparing the updated state of the user's heart rate with an expected range for user's heart rate. The expected range of the user's heart rate may be one determined based upon circadian variations in heart rate. An example of a circadian variation in heart rate may include dipping in heart rate during the night. Thus, depending upon the time of day that the updated heart rate is measured from the sensor data, the system adjusts the acceptable heart rate range for the user based upon location within the circadian cycle to which the measurement time corresponds. This may mean that the expected heart rate range is increased, decreased, or left unchanged based upon the time of day that the updated state of the heart rate biological marker is determined.

In another example, the system is capable of comparing the updated state of the user's blood pressure with an expected range for the user. The expected range may be adjusted based upon circadian variations in blood pressure. Examples of circadian variations in blood pressure include morning surge reactivity and dipping in blood pressure during the night. Thus, depending upon the time of day that the updated blood pressure is measured, the system adjusts the acceptable blood pressure range for the user based upon the location within the circadian cycle to which the measurement corresponds.

In another aspect, the system accounts for medication characteristics. In one example, the system evaluates the updated state of the biological marker in view of circadian variation for the biological marker and/or in view of the medication characteristics such as half-life. The system is capable of determining whether, based upon the data indicating the time that the medication was taken, whether the medication is still active within the user's body. This determination is applied to the analysis of whether the updated state of the biological marker for the user is within the expected range for the user which may include an applied circadian variation.

For example, the system is capable of marking a time period that starts with a dose time for a medication. The dose time may be determined from a received user input indicating that a dose of a medication was taken, from the regimen for the user specifying expected dose times, etc. The end of the time period may be an amount of time after the dose time that corresponds to, or equals (e.g., approximately equals) the half-life of the medication. The system is capable of determining whether a detected change in a biological marker regulated by the medication occurs within that time period.

Thus, if the biological marker for the user has changed compared to the baseline and/or is out of range (e.g., given circadian variations) and the medication influencing the biological marker is no longer within the user's body in sufficient quantity to have the desired effect upon the biological marker (e.g., based upon half-life), the system may log the timing discrepancy. Similarly, if the biological marker for the user has changed compared to the baseline and/or is out of range and the system determines that the medication influencing the biological marker is still within the user's body in sufficient quantity to have the desired effect upon the biological marker (e.g., based upon half-life), the system may log the timing discrepancy.

A detected change during the time period that the medication should still be active is an indication that the medication may not be working as expected. In an example, the system may generate a record that the biological marker for the user is out of the expected range given circadian variation. In another example, the system may generate a record indicating whether the medication, at the time of measurement of the updated state of the biological marker, is within the user's body in sufficient quantity based upon half-life. In another example, the system may indicate the half-life of the medication, any change or deviation from an expected value in the biological marker correlated with the medication, and the dose time.

In another aspect, the system is capable of performing a continual (e.g., 24 hour by 7 day a week) analysis of stress for the user. The system is capable of flagging particular days and/or time segments of days (e.g., early-morning, morning, late night, etc.) where stress exceeds a baseline amount of stress by more than a threshold amount. Detecting high levels of stress allows the system to more accurately and reliably monitor health of the user to detect chronotherapeutic effects through examination of heart rate and/or in situations where continual blood pressure monitoring is not feasible. The system is further capable of determining how quickly a person recovers from a stress episode using heart rate variability data. Heart rate variability resilience, for example, indicates how quickly the user recovers from the stress episode.

In another illustrative example, the system is capable of detecting one or more biological markers relating to psychological health. For example, the system is capable of determining an updated, or current, mood and/or an updated, or current, state of depression for the user. As discussed, the system is capable of detecting a level of depression based upon voice analysis, heart rate and heart rate variability, user provided data, and so forth. The system is capable of comparing the current updated state of mood and/or depression with baselines of mood and/or depression.

In another illustrative example, the system is capable of evaluating biological markers, e.g., the updated state of the biological markers, to determine whether the biological markers are consistent with the expected circadian variations in a healthy body. For instance, the system is capable of evaluating the dipping/non-dipping phenomenon during the night and/or morning surge reactivity for the user. A worsening of these patterns, or the departure of one or both of these patterns, from the patterns expected in a healthy human body (e.g., of same or similar age as the user) indicates a problem with the medication regimen (e.g., patient error or error in prescribing), the nature of the medications (e.g., family of drugs), the formulation of the medications (e.g., extended release), dosing strength of the medications, etc.

The system is also capable of using various biological markers to determine trends in health status for the user. For example, since heart rate variability biological markers are computed, the system is capable of determining whether the patterns observed are consistent with an improvement in ANS functions even without computing blood pressure. As another example, because the system is capable of computing biological markers for depression, the system is also capable of determining whether the psychological health of the user is affected by the medication regimen. The system determines that increasing (decreasing) intensity of biological markers for depression indicate a worsening (improvement) of psychological health for the user. In another example, the system is capable of calculating total activity of the user. Total activity of the user may be determined or calculated based upon accelerometer data, e.g., output power (e.g., wattage). Thus, in one aspect, the system is capable of analyzing trends in total activity where lower levels or decreasing trends in total activity of the user are interpreted as a worsening of joint pain for the user.

In block 355, the system is capable of providing a notification of results obtained from the analysis described with reference to block 345 and/or block 350. In one aspect, the system is capable of providing a notification of the result to the user. For example, the system may provide a visual message on the display screen of the system, an audible message, etc. In another aspect, the system is capable of providing a notification to a medical service provider. For example, the system may send an electronic mail, a text message or instant message, or the like to a medical service provider device or system indicating that one or more biological markers are out of range, vary from the baseline by a statistically significant amount, etc. It should be appreciated that the system may also be configured to provide notifications, e.g., status updates, even in cases where the analyzed biological markers are within expected ranges. Based upon the information provided within the notifications, a medical service provider may adjust one or more of the medications of the regimen for the user.

In one or more embodiments, the system is also capable of detecting dyssynchrony in ▫ the user. Dyssynchrony refers to a condition in which the environmental cues and patterns, such as sleeping and eating, conflict with the user's existing patterns. By detecting dyssynchrony using sensor data, the medication regimen for the user may be varied. For example, when the user is in a state of dyssynchrony with respect to circadian rhythm, e.g., due to irregular sleep time, medications with higher half-life should be given so as to remain in the user's system throughout the irregular sleep cycle. The system is capable of detecting dyssynchrony such as an irregular sleep pattern and determining whether the half-life of a prescribed medication is long enough to moderate a biological marker influenced by the medication.

In an embodiment, the system is capable of establishing dyssynchrony by examining regularity of sleep time and thus the timing and the length of the awake/sleep cycle. The system is capable of determining covariances between circadian ANS and endocrinological biological markers with expected circadian rhythm to determine any unexpected unhealthy trend. The endocrinological biological markers, for example, may include morning surge reactivity. The system is capable of providing results of analysis to a medical service provider, e.g., a device or system thereof, to facilitate the chronotherapeutic adjustment of the medication regimen of the user based on the half-life of the medications taken and/or based upon the prescribing physician. Further, the results of the analysis allow a medical service provider to verify the correctness of any adjustments made to the regimen.

Figure 4:
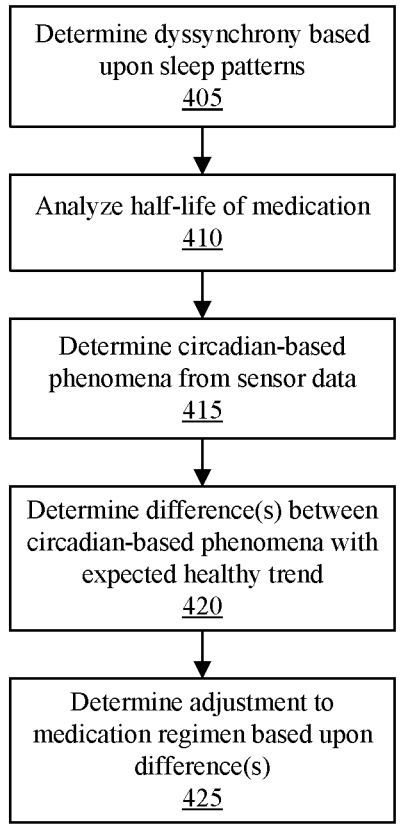
FIG. 4 illustrates another example method of chronotherapeutic dosing.

FIG. 4 illustrates another example method 400 of chronotherapeutic dosing. Method 400 can be performed by a system the same as or similar to the system described in connection with FIG. 1. Method 400 incorporates the detection of dyssynchrony as described above.

In block 405, the system determines whether the user's daily profile exhibits dyssynchrony. In one aspect, the system is capable of analyzing sleep patterns using the sensor data. The system is capable of determining whether the user sleeps through the night, is up at one or more times throughout the night, the time periods during which the user sleeps, and so forth. For example, the system determines the regularity of the user's sleep and whether the user sleep pattern coincides with circadian rhythm.

In block 410, the system analyzes the half-life of one or more medications taken by the user. In block 415, the system determines one or more circadian-based phenomena for the user from the sensor data. For example, from the sensor data, the system is capable of determining whether the user exhibits dipping or non-dipping phenomena, morning surge, and so forth. Further, the system is capable of determining whether the circadian-based phenomena occur within the half-life of the particular medication intended to regulate the phenomena. For example, the system is capable of determining whether dipping or non-dipping occurs during the time that heart rate and/or blood pressure is to be regulated by a particular medication or medications. As discussed within this disclosure, the time(s) that the user takes a dose of a medication may be determined by the system by reading the medication regimen and/or from received user inputs specifying such data.

In block 420, the system is capable of determining differences between circadian-based phenomena (e.g., as measured from the sensor data) and expected healthy trends in the measured circadian-based phenomena. An expected healthy trend specifies the circadian variation in one or more biological markers for a healthy individual (e.g., human being). In one example, the system is capable of determining whether the measured circadian-based phenomena differ from the expected healthy trends by more than a threshold amount. The difference may be measured in any of a variety of ways including, but not limited to, covariance between two markers which may be classified as ANS markers and those which may be classified as endocrinological markers. Using the difference analysis, the system is capable of detecting an unexpected unhealthy trend. For example, detecting a difference that exceeds a threshold amount is indicative of an unhealthy trend.

In block 425, the system is capable of determining, e.g., suggesting, an adjustment to the medication regimen based upon characteristics of medications as determined from the medication database. For example, the system is capable of indicating whether the medication is achieving a goal based upon the detected difference in block 420. In another example, the system is capable of recommending an accepted alternative to a medication where the accepted alternative has a longer half-life than the medication being replaced in cases where the analysis indicates dyssynchrony. In another example embodiment, the system is capable of providing the results of any analysis to a medical service provider to aid the provider in adjusting the medication timing, dosage, and/or type of medication.

In one or more embodiments, the processing of the biological markers can be used for real-time identification of optimal conditions or timing for dosing. For example, the system can monitor the biological markers for particular physiological condition(s) considered to be optimal or beneficial for consuming a particular medication on the medication regimen for the user. In response to detecting the physiological condition(s), the system is capable of notifying the user to take a certain dosage of medication. If such a condition is not detected within a timeframe, the device can alert the user to take the medication so that a minimum dosage level is achieved (e.g., 2× daily).

Adherence to a medication regimen can be a significant problem for patients. This is particularly true for cardiac patients suffering from heart failure. Given the impaired pumping capability of the heart, possible congestion in the cardiovascular system, and extracellular matrix, missing a dose of medication for only a few days have adverse effects. As an illustrative example, failure to adhere to a medication regimen can be particularly dangerous for patients suffering from NYHA Class II, III, or IV heart failure.

A number of medications given during cardiac dysfunctions directly influence the ionotropy, chronotropy, or lusitropy of the heart. As such, many of these medications influence sympathetic tone, blood pressure, heart rate variability, etc. Likewise, diuretics may be given to directly influence the ANS of the user, e.g., the sympathetic and parasympathetic nervous systems. Beta blockers are one example type of medication that affects both ionotropy and chronotropy of the heart. Other medications can influence a user's blood pressure by working on a complementary part of endocrinological systems. An example such as blood pressure medication inhibits the RAS, which directly reduces blood pressure. ACE-inhibitors or ARBs (angiotensin receptor blockers) are drugs of this family are known to lead to a reduction of blood pressure.

For reasons described above and to decrease the ionotropy of the heart (e.g., to decrease the force of contraction and thus the stress on the heart), a number of medication regimens that include beta blockers may be enforced on the patient. Beta blockers directly inhibit the function of beta-adrenergic receptors and thus the catecholamine uptake, and consequent changes in heart rate, preferably during the night, to better control the night-time as well as day time blood pressure.

As previously discussed, blood pressure can be synchronized in a predictable manner with the circadian rhythm and the rhythm of the user's activity-rest cycle. Other physiological functions, such as renal, cardiovascular, gastrointestinal, and endocrinological functions, also can undergo a circadian pattern. Other circadian-based phenomena such as the CAR and heart rate and blood pressure dipping at night may be managed and/or created within the user through proper medication regimen for purposes of improved health.

For the foregoing reasons, among others, adhering to a medication regimen is of utmost importance for many patients. Many patients, however, suffer from multiple comorbidities. These patients are likely to have more complex medication regimens where larger quantities of medications are to be consumed at several different times during the day. This complexity may be a hurdle for medication regimen adherence.

Figure 5:
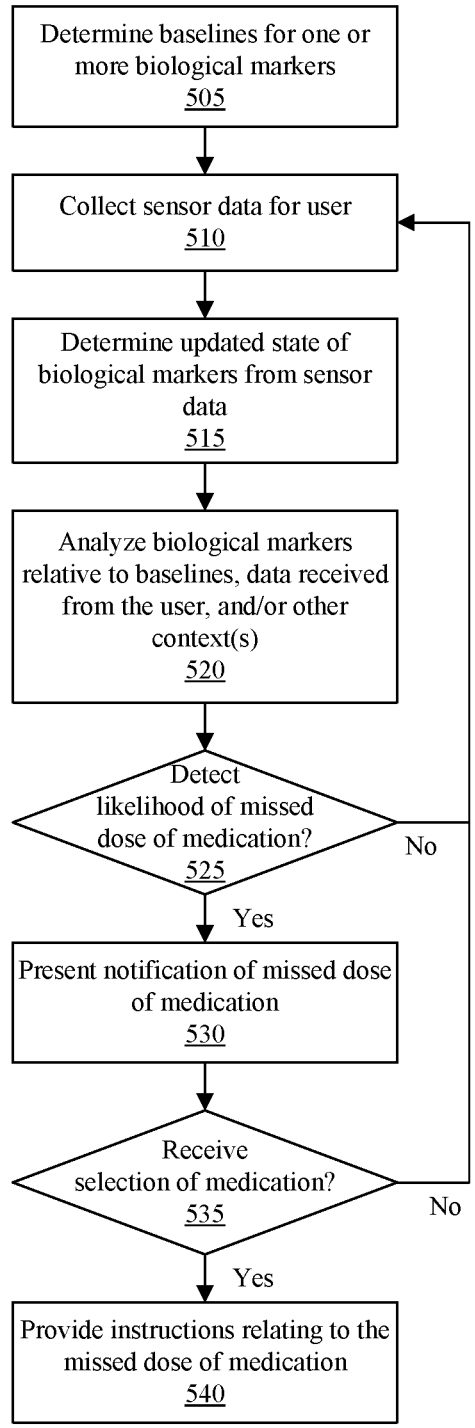
FIG. 5 illustrates an example method of analyzing user adherence to a medication regimen.

FIG. 5 illustrates an example method 500 of analyzing user adherence to a medication regimen. For example, method 500 may be used to determine whether a user has missed a dose of a medication. Method 500 may be performed by a system the same as or similar to the system described in connection with FIG. 1.

In block 505, the system is capable of determining baselines for one or more biological markers. The system is capable of determining baselines for one or more biological markers as discussed in connection with FIG. 2. Once determined, the system stores the baselines for the biological markers within a memory for subsequent use.

In one or more embodiments, the system is also capable of establishing baselines for physiological states such as ionotropy, chronotropy, dromotropy, and/or blood volume. Ionotropic state indicates the strength of contraction of the user's heart muscle. In one aspect, the system is capable of measuring ionotropic state from blood pressure data and PPG morphology. As discussed, the system is capable of determining systolic blood pressure for a user based upon the area beneath the curve of a PPG waveform.

Chronotropic state refers to the heart rate and rhythm of the user's heart. Thus, in one aspect, the system is capable of measuring heart rate as an indicator of chronotropic state. Dromotropic state refers to the conduction speed of the atrioventricular node, which is part of the electrical conduction system, in the user's heart. The system is capable of measuring dromotropic state through an analysis of PPG morphology and, further, may measure dromotropic state through an analysis of PPG morphology combined with ECG information. The system is capable of measuring beta receptor blockage using heart rate variability. The system is further capable of measuring blood volume using PPG morphology and/or AUC.

In block 510, the system is capable of collecting sensor data for the user. As discussed, the system is capable of collecting sensor data continuously throughout the day over many days. In block 515, the system is capable of calculating updated states of the biological markers from the sensor data.

In block 520, the system is capable of analyzing the biological markers relative to the baselines, data received from the user, and/or other context(s). In an aspect, the system compares the updated states of the biological markers as determined from the sensor data with the previously computed baselines to determine whether a change is detected. In an aspect, a change is a statistically significant difference such as a difference that exceeds a threshold amount.

For example, given a stable contextual baseline of ANS measurements, e.g., stress and heart rate, the system may perform a missed drug analysis as follows. The system is capable of analyzing the updated state of the biological markers and/or physiological states for an anomaly compared to the baseline biological marker(s) and/or baseline physiological state(s) (e.g., a baseline where the user adheres to the medication regimen). In response to the system determining that an updated state of a biological marker and/or physiological state varies from the baseline by an amount exceeding a threshold amount, the system determines that a likelihood exists that a dose of a medication that regulates the analyzed biological marker and/or physiological state has been missed. The system is capable of generating a record stored therein indicating a likely missed dose of a medication from the medication regimen that regulates the analyzed biological marker.

In an embodiment, the system is also capable of determining that a detected change in a biological marker and/or physiological state is correlated with a dose time for a medication based upon the regimen and/or data entered into the system indicating the dose time for the medication. For example, the system is capable of determining that a change detected in a time period starting from the dose time and ending at the half-life of the medication (e.g., a time approximately a half-life of the medication measured from the dose time) indicates that the dose of the medication was not taken by the user. The system may determine half-life information for medications from the medication database described herein.

In one or more embodiments, the system is capable of making a determination that a dose of a medication was likely missed using other, additional information. For example, the system may receive additional data from the user. The user, for example, may access a user interface presented by the system to enter information such as times when particular medications are taken. To avoid an incorrect determination that a user missed a dose of a medication, in one aspect, the system only makes such a determination in response to detecting a variance above a predetermined threshold of an updated state of a biological marker and/or physiological state and the relevant or same baseline accompanied by a lack of an entry indicating that the user took one or more medications at a prescribed time that coincides with the variance analysis.

In one or more other embodiments, the system is capable of making a determination that a dose was likely missed based upon whether indicators of an autonomic disturbance have been detected. For example, in response to detecting a variance as described above and that no indicators of an autonomic disturbance have been detected, the system is capable of determining that a dose of a medication was missed. In an aspect, the system is capable of detecting indicators for autonomic disturbances that may be independently confirmed. For example, the system is capable of using user-application interaction, activity analysis, facial feature analysis using a camera of the system, voice tone analysis, and so forth to detect whether an autonomic disturbance has occurred. In the case where an indication of an autonomic disturbance is detected, the system is unable to attribute the variance in the updated state of the biological marker to a missed dose of medication.

The system is also capable of evaluating one or more contexts relating to the user. For example, the system is capable of determining movements, quality of sleep, and/or other activities of the user from an analysis of sensor data. As an illustrative example, the system may evaluate accelerometer data to detect movements of the user. In another illustrative example, the system may evaluate accelerometer data and/or location data to determine whether user is making trips to the bathroom and/or the frequency of such trips.

The system is capable of using any of the foregoing techniques individually or in any combination to determine whether a dose of a medication was missed by the user. In another example, the system may continue to calculate updated states of biological markers over time and continue to perform the comparisons and analysis described above. The system is capable of correlating the times at which changes are detected in biological markers with times that medications are to be taken per the regimen and/or with the half-lives of the medications.

Given the timing analysis, the system is also capable of determining that the updated state of one or more biological markers described above returns to an expected state, e.g., no longer deviates from the baseline by more than the threshold amount, albeit at a time later than expected. In that case, the delayed response in the updated state of the biological markers indicates that a dose of medication was likely taken later than the prescribed time in accordance with the medication regimen.

For purposes of illustration, consider the following examples of missed drug analysis that may be performed by the system using the various biological markers and/or contexts described herein. In an example, the system is capable of detecting a missed dose of a diuretic medication by determining that a diuretic medication is on the regimen for the user and also detecting an increase by at least a threshold amount in PPG AUC (area under curve) between the updated state of the biological markers and the baseline, in combination with decreased trips to the bathroom (or decreased frequency of trips) based upon accelerometer data and/or location data.

In another example, the system is capable of detecting a missed dose of a calcium channel blocker medication. The system is capable of detecting a missed dose of a calcium channel blocker medication by determining that a calcium channel blocker medication is listed on the regimen for the patient and also detecting an increase in vascular transit time (VTT).

In another example, the system is capable of detecting a missed dose of an arrhythmia medication. The system is capable of detecting a missed dose of an arrhythmia medication by determining that an arrhythmia medication is listed on the regimen for the patient and from evaluation of ECG morphology.

In another example, the system is capable of detecting a missed dose of an antidepressant medication. The system is capable of detecting a missed dose of an antidepressant medication by determining that an antidepressant medication is listed on the regimen for the patient and from evaluation of tone of the user's voice, heart rate, heart rate variability, user provided input data, etc. In one aspect, the system is capable of detecting a missed dose of an antidepressant in response to detecting a change where the user's heart rate and the user's heart rate variability both are low, e.g., by at least a threshold amount, compared to the relevant baselines.

In another example, the system is capable of detecting a missed dose of a Parkinson's medication. The system is capable of detecting a missed dose of a Parkinson's medication by determining that a Parkinson's related medication is listed on the regimen for the patient and from evaluation of accelerometer data indicating an increase in tremors of the user.

In another example, the system is capable of detecting a missed dose of a pain and/or arthritis medication. The system is capable of detecting a missed dose of a pain and/or arthritis medication by determining that a pain and/or arthritis related medication is listed on the regimen for the patient and from evaluation of accelerometer data indicating a change (e.g., by at least a threshold amount) in the gait of the user compared to a baseline.

In another example, the system is capable of detecting a missed dose of a sleep medication. The system is capable of detecting a missed dose of a sleep medication by determining that a sleep related medication is listed on the regimen for the patient and from detecting reduced quality of sleep and/or sleep restlessness based upon accelerometer data, heart rate data, etc. varying from baselines by at least a threshold amount during time periods when the user is supposed to be sleeping.

In one or more embodiments, the system is also capable of determining that a dose of a medication was taken later than the prescribed time, per the regimen, in response to detecting a delayed response in one or more ANS biological markers. As an illustrative example, the system may detect a delayed dipping and/or non-dipping syndrome, a delayed morning surgery activity, or the like.

Due to the impracticality of continuously monitoring blood pressure, the system is capable of utilizing other alternatives. In the case of beta blockers, however, continuous monitoring of heart rate does not always indicate the effect of beta blockers due to sympathetic system overdrive due to physiological stress. Sympathetic system overdrive due to physiological stress can act in direct opposition to the effect of beta blockers. This makes detection of a missed dose of a beta blocker problematic. Further the lack of escalation in heart rate can, at times, be a marker of depression. Thus in the absence of a blood pressure measurement, heart rate alone is not a reliable indicator of missed beta blockers.

Accordingly, in one or more embodiments, the system is capable of supplementing the ANS measurements with heart rate variability measurements. Supplementing the ANS measurements with heart rate variability measurements allows the system to detect instances where the heart rate is high but the cause is due to stress levels exceeding a particular threshold. In such cases, the system determines that heart rate is high not due to a missed dose of a medication, but rather due to stress thereby avoiding a false alarm. The system further is capable of performing a covariance analysis of heart rate and heart rate variability to rule out cases where the change in expected heart rate is due to a stress episode.

In another example, the system is capable of detecting impaired heart rate variability and reduction in heart rate concomitant with a user's indication of depression through one or more user inputs provided to the system and/or other depression detection techniques described herein. In that case, the system determines that the lowering of heart rate variability and the lowering of heart rate is a marker for depression rather than an effect of having taken a beta blocker medication.

In block 525, based upon the foregoing analysis, the system determines whether a dose of the medication is likely missed. In response to determining that a dose of the medication is likely missed, method 500 continues to block 530. In response to determining that a dose of the medication is likely not missed, method 500 loops back to block 510 to continue processing.

In block 530, the system is capable of presenting a notification of the missed dose of medication. In an embodiment, the system displays a user interface and a notification that the particular medication correlated with the biological marker exhibiting a change or variance was likely missed. In an aspect, the notification may include an image of the particular medication determine to be missed. For example, the system may present a graphic image of a pill or other medication for which the system determines a dose was likely missed by the user.

In one or more embodiments, the system is capable of providing the notification to a medical service provider. For example, the system is capable of sending a message to a system and or device of a medical service provider indicating that the user likely skipped a dose of the medication.

While method 500 illustrates an example implementation where notifications and/or images of medications are presented in response to a determination that the user has likely missed a dose of a medication, in one or more other embodiments, the system is capable of providing notifications to the user throughout the day. For example, the system may provide reminders or other notifications prior to scheduled times when the user is to take one or more particular medications. Notifications, for example, may be pushed to a user's mobile phone at different times during the day. As part of the notifications, the system may provide graphic images of the particular medications the user is to take. The distinctive shapes and colors of most medications may help the user in remembering which medications are to be taken at a given point in time.

In block 535, the system determines whether a selection of a medication has been received. For example, the system determines whether a listing of a medication and/or a graphic image of a particular medication presented in block 530 has been selected by way of a received user input. In response to a selection of the medication, method 500 proceeds to block 540. In response to no selection of the medication or selection of an option to dismiss the notification, method 500 can loop back to block 510 to continue processing.

In block 540, the system is capable of providing instructions relating to the missed dose of medication. In one example, the system is capable of providing instructions as to when and how much of the medication should be taken in consequence of the missed dose.

In an embodiment, the system is capable of presenting a user interface asking the user to confirm whether or not medications determined to have been skipped by the system were taken by the user. In cases where the system determines that the user has not taken a dose of the medication and/or where the user affirms that a dose of the medication was skipped, the system is capable of providing further instructions as to when a next dose should be taken and/or the amount of such next dose. If a drug/medication missed is of an urgent nature, the system is capable of sending a warning message, which may include an audiovisual message, to the user and/or his care providers. In an embodiment, particular medications may be flagged as critical, e.g., within the medication database.

In an embodiment, in response to a determination that the user skipped a dose of the medication and/or a response from the user affirming that the user skipped a dose of the medication, the system is capable of scheduling a reminder to provide to the user to take a dose of the medication.

In some cases, the medication regimen for a user calls for the user to take more than one medication at the same time of day. For example, user may be required to consume one or more medications in the morning and or one or more medications in the evening. In an embodiment, in response to determining that the user likely skipped a dose of a selected medication at a particular time, the system may make a further determination that the user likely skipped doses of other medications that were to be consumed by the user at the same time as the selected medication based upon the medication regimen for the user. In that case, the system may provide further notifications relating to the other medications believed to be skipped by the user. The system may also provide further notifications to medical service providers indicating that the user likely skipped the selected medication and/or the other medications scheduled for consumption by the user at the same time as the selected medication. The example embodiments described herein are applicable to medications taken in any of a variety of different forms, e.g., as inhalers, in liquid form, in pill form, etc.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise.

As defined herein, the term "another" means at least a second or more.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, or the like.

As defined herein, the terms "one embodiment," "an embodiment," "one or more embodiments," or similar language mean that a particular feature, structure, or characteristic described in connection with the embodiment is included in at least one embodiment described within this disclosure. Thus, appearances of the phrases "in one embodiment," "in an embodiment," and similar language throughout this disclosure may, but do not necessarily, all refer to the same embodiment. The terms "embodiment" and "arrangement" are used interchangeably within this disclosure.

As defined herein, the term "output" means storing in physical memory elements, e.g., devices, writing to display or other peripheral output device, sending or transmitting to another system, exporting, or the like.

As defined herein, the term "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "user" means a human being. The term "patient" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method of chronotherapeutic dosing, comprising:
generating sensor data corresponding to a user using one or more sensors of a device, wherein the sensor data is generated subsequent to the user starting a regimen for a medication;
detecting, using a processor of the device, dyssynchrony in sleep of the user based on a comparison of a sleep pattern of the user, determined from the sensor data, with a circadian rhythm for sleep;
determining, from a medication database and using the processor, a half-life of the medication, wherein the medication regulates a circadian-based phenomenon;
determining, using the processor, the circadian-based phenomenon for the user from the sensor data, wherein the circadian-based phenomenon is determined from a biological marker including at least one of blood pressure or heart rate;
determining, using the processor, that the circadian-based phenomenon does not occur during the half-life of the medication based on a dose time of the medication for the user, wherein the circadian-based phenomenon is dipping of at least one of heart rate or blood pressure during night;
comparing, using the processor, the circadian-based phenomenon with an expected healthy trend of the circadian-based phenomenon retrieved from a circadian variation database thereby determining a difference between the circadian-based phenomenon and an expected healthy trend, wherein the difference exceeds a threshold and occurs outside of the half-life of the medication; and
in response to detecting the dyssynchrony in sleep of the user and determining the difference, providing, using the processor, a notification of the difference;
wherein the notification is generated to recommend an alternative medication that regulates the biological marker, wherein the alternative medication has a longer half-life than the medication.

2. The method of claim 1, wherein the circadian-based phenomenon includes morning surge reactivity in the user.

3. A system for chronotherapeutic dosing, comprising:
one or more sensors configured to generate sensor data corresponding to a user, wherein the sensor data is generated by the one or more sensors subsequent to the user starting a regimen for a medication;
a memory storing instructions; and
a processor coupled to the sensor and the memory, wherein the processor, in response to executing the instructions, is configured to initiate executable operations including:
detecting dyssynchrony in sleep of the user based on a comparison of a sleep pattern of the user, determined from the sensor data, with a circadian rhythm for sleep;
determining, from a medication database, a half-life of the medication, wherein the medication regulates a circadian-based phenomenon;
determining the circadian-based phenomenon for the user from the sensor data, wherein the circadian-based phenomenon is determined from a biological marker including at least one of blood pressure or heart rate;
determining, using the processor, that the circadian-based phenomenon does not occur during the half-life of the medication based on a dose time of the medication for the user, wherein the circadian-based phenomenon is dipping of at least one of heart rate or blood pressure during night;
comparing, using the processor, the circadian-based phenomenon with an expected healthy trend of the circadian-based phenomenon retrieved from a circadian variation database thereby determining a difference between the circadian-based phenomenon and an expected healthy trend, wherein the difference exceeds a threshold and occurs outside of the half-life of the medication; and in response to detecting the dyssynchrony in sleep of the user and determining the difference, providing a notification of the difference;

wherein the processor is configured to generate the notification to recommend an alternative medication that regulates the biological marker, wherein the alternative medication has a longer half-life than the medication.

4. The system of claim 3, wherein the circadian-based phenomenon includes morning surge reactivity in the user.

5. A computer program product comprising a non-transitory computer readable storage medium having program code stored thereon, the program code executable by a processor to perform operations for chronotherapeutic dosing comprising:

receiving sensor data corresponding to a user, wherein the sensor data is generated by one or more sensors of a device and is generated subsequent to the user starting a regimen for a medication;

detecting dyssynchrony in sleep of the user based on a comparison of a sleep pattern of the user, determined from the sensor data, with a circadian rhythm for sleep;

determining, from a medication database, a half-life of the medication, wherein the medication regulates a circadian-based phenomenon;

determining the circadian-based phenomenon for the user from the sensor data, wherein the circadian-based phenomenon is determined from a biological marker including at least one of blood pressure or heart rate;

determining that the circadian-based phenomenon does not occur during the half-life of the medication based on a dose time of the medication for the user, wherein the circadian-based phenomenon is dipping of at least one of heart rate or blood pressure during night;

comparing the circadian-based phenomenon with an expected healthy trend of the circadian-based phenomenon retrieved from a circadian variation database thereby determining a difference between the circadian-based phenomenon and an expected healthy trend, wherein the difference exceeds a threshold and occurs outside of the half-life of the medication; and in response to detecting the dyssynchrony in sleep of the user and determining the difference, providing a notification of the difference;

wherein the notification is generated to recommend an alternative medication that regulates the biological marker, wherein the alternative medication has a longer half-life than the medication.

6. The computer program product of claim 5, wherein the circadian-based phenomenon includes morning surge reactivity in the user.

* * * * *